(12) United States Patent
Matzinger et al.

(10) Patent No.: US 8,391,940 B2
(45) Date of Patent: Mar. 5, 2013

(54) METHODS AND SYSTEMS TO CORRECT FOR HEMATOCRIT EFFECTS

(75) Inventors: David P Matzinger, Menlo Park, CA (US); Geoffrey McGarraugh, San Francisco, CA (US); Jerry T Pugh, Santa Rosa, CA (US)

(73) Assignee: LifeScan, Inc., Milpitas, CA (US)

( * ) Notice: Subject to any disclaimer, the term of this patent is extended or adjusted under 35 U.S.C. 154(b) by 514 days.

(21) Appl. No.: 12/700,461

(22) Filed: Feb. 4, 2010

(65) Prior Publication Data
US 2011/0190607 A1 Aug. 4, 2011

(51) Int. Cl.
*A61B 5/00* (2006.01)

(52) U.S. Cl. ....................................................... 600/316

(58) Field of Classification Search ................... 600/316
See application file for complete search history.

(56) References Cited

U.S. PATENT DOCUMENTS

| | | | |
|---|---|---|---|
| 5,179,005 A | 1/1993 | Phillips et al. | |
| 5,780,304 A | 7/1998 | Matzinger et al. | |
| 5,789,255 A | 8/1998 | Yu | |
| 5,968,836 A | 10/1999 | Matzinger et al. | |
| 6,391,645 B1 * | 5/2002 | Huang et al. | 436/95 |
| 2003/0054427 A1 * | 3/2003 | Phillips et al. | 435/14 |
| 2004/0157275 A1 | 8/2004 | Marfurt | |
| 2009/0098657 A1 | 4/2009 | Blais et al. | |
| 2009/0292489 A1 * | 11/2009 | Burke et al. | 702/65 |
| 2009/0301899 A1 * | 12/2009 | Hodges et al. | 205/777.5 |

OTHER PUBLICATIONS

International Search Report, PCT Appln. No. PCT/US2011/023545, dated Apr. 27, 2011, 5 pages, Rijswijk, Netherlands.

* cited by examiner

*Primary Examiner* — Clayton E Laballe
*Assistant Examiner* — Dennis Hancock

(57) ABSTRACT

Described and illustrated herein are exemplary methods of operating an analyte measurement system having a meter and a test strip. Such methods may be exemplarily achieved by determining a first glucose concentration by measuring a first reflectance at about a first wavelength at a testing surface of the pad; measuring a second reflectance at about a second wavelength; formulating at least one equation to correct the first glucose concentration for temperature or hematocrit effects using the second reflectance at about the second wavelength; determining a second glucose concentration using the first glucose concentration, the second reflectance at about a second wavelength; and displaying the second glucose concentration that is corrected for temperature and hematocrit effects.

8 Claims, 8 Drawing Sheets

US 8,391,940 B2

METHODS AND SYSTEMS TO CORRECT FOR HEMATOCRIT EFFECTS

BACKGROUND

Measuring the concentration of substances, particularly in the presence of other substances, is important in many fields, and especially in medical diagnostics. For example, the measurement of glucose in body fluids, such as blood, is crucial to the effective treatment of diabetes.

Proper regulation of blood glucose fluctuations requires accurate measurement of the concentration of glucose in the blood. Failure to do so can produce extreme complications such as blindness and loss of circulation in the extremities.

Multiple methods are known for measuring the concentration of glucose in a blood sample. Such methods typically fall into one of two categories: optical methods and electrochemical methods. Optical methods generally involve the use of reflectance or absorbance spectroscopy to determine the glucose concentration. In optical methods, a chemical reaction produces a color change indicative of the concentration of glucose. Electrochemical methods generally involve measuring amperometric or coulometric responses that are proportional to the concentration of glucose.

Multiple contributing factors, such as variations in blood composition, limit the accuracy of blood glucose measurements. For example, variations in hematocrit, the concentration of red blood cells, can affect the signal generated by the interaction of a blood sample with the test reagent. Variations in the temperature at which the glucose is measured may also affect the accuracy of the blood glucose result.

SUMMARY OF THE DISCLOSURE

Applicants have recognized a need for a system and method that can accurately measure blood glucose in the presence of varying temperature and hematocrit.

In view of the foregoing and in accordance with one aspect, there is provided a method of correcting for hematocrit effects in a glucose measurement system having a meter and a test strip. The test strip includes a pad sandwiched between a transport medium and a support. The pad is impregnated with color-producing reagent. The meter includes optical components configured to direct light at a testing surface of the test strip and to measure the reflected light from the testing surface of the test strip. The meter also includes a signal processor configured to process the reflected light from the testing surface and to calculate a glucose concentration that is corrected for temperature and hematocrit effects. The method can be achieved by: determining a first glucose concentration by measuring a first reflectance at about a first wavelength proximate a surface of the test strip having a membrane impregnated with a color-producing reagent; measuring a temperature and a second reflectance at about a second wavelength; determining a second glucose concentration with at least one equation to correct the first glucose concentration with the temperature and the second reflectance at about the second wavelength; and displaying the second glucose concentration.

In yet a further embodiment, a method of correcting a glucose concentration in a glucose measurement system. The system includes a test strip and an optical reading device. The method can be achieved by: determining a first glucose concentration by measuring a first reflectance at about a first wavelength proximate a surface of the test strip having a membrane impregnated with a color-producing reagent; measuring a second reflectance at about a second wavelength; determining a second glucose concentration with at least one equation based on the second reflectance at about the second wavelength; and displaying the second glucose concentration.

In another embodiment, a method of correcting a glucose concentration in a glucose measurement system. The system includes a test strip and an optical reading device. The method can be achieved by: determining a first glucose concentration by measuring a first reflectance at about a first wavelength proximate a surface of the test strip having a membrane impregnated with a color-producing reagent; measuring a second reflectance at about a second wavelength; determining a second glucose concentration based on the second reflectance at about the second wavelength with an equation of the form:

$$G2 = a0 + a1*G1 + a2*K/S_{\lambda 2} + a3*G1*K/S_{\lambda 2} + a4*(G1)^2 + a5*(K/S_{\lambda 2})^2 + a6*(G1)^3 + a7*(K/S_{\lambda 2})^3 a8*(G1)^2*(K/S_{\lambda 2}) + a9*G1*(K/S_{\lambda 2})^2$$

where:
G2 is the second glucose concentration corrected for temperature and hematocrit effects;
G1 is the first glucose concentration and is determined from the first reflectance measured at about a first wavelength, $\lambda 1$;
$K/S_{\lambda 2}$ comprises a value obtained with an equation of the form:

$$K/S_{\lambda 2} = (1-R_2)^2/(2*R_2)$$

where:
$R_2$ is the second reflectance at about the second wavelength, $\lambda 2$, taken at an endpoint time; and
Coefficients a0 through a9 depend on the endpoint time at which
the reflectance at about the first wavelength, $\lambda 1$, is measured; and displaying the second glucose concentration.

In another embodiment, a method of correcting a glucose concentration in a glucose measurement system. The system includes a test strip and an optical reading device. The method can be achieved by: determining a first glucose concentration by measuring a first reflectance at about a first wavelength proximate a surface of the test strip having a membrane impregnated with a color-producing reagent; measuring a temperature and a second reflectance at about a second wavelength; determining a second glucose concentration based on the temperature and the second reflectance at about the second wavelength with an equation of the form:

$$G2 = a0 + a1*G1 + a2*T + a3*K/S_{\lambda 2} + a4*G1*T + a5*G1*K/S_{\lambda 2} + a6*T*K/S_{\lambda 2} + a7*(G1)^2 + a8*(T)^2 + a9*(K/S_{\lambda 2})^2 + a10*(G1)^3 + a11*(T)^3 + a12*(K/S_{\lambda 2})^3 + a13*G1*T*K/S_{\lambda 2} + a14*(G1)^2*T + a15*(G1)^2*(K/S_{\lambda 2}) + a16*G1*T^2 + a17*G1*(K/S_{\lambda 2})^2 + a18*T*(K/S_{\lambda 2})^2 + a19*T^2*(K/S_{\lambda 2})$$

where:
G2 is the second glucose concentration corrected for temperature and hematocrit effects;
G1 is the first glucose concentration and is determined from the reflectance measured at about a first wavelength, $\lambda 1$;
T is temperature;
$K/S_{\lambda 2}$ comprises a value obtained with an equation of the form:

$$K/S_{\lambda 2} = (1-R_2)^2/(2*R_2)$$

where:
$R_2$ is the second reflectance at about the second wavelength,
$\lambda 2$, taken at an endpoint time; and Coefficients a0 through a19 depend on the endpoint time at which the first reflectance at about the first wavelength, $\lambda 1$, is measured; and displaying the second glucose concentration.

In yet still another embodiment, a method of correcting a glucose concentration in a glucose measurement system. The system includes a test strip and an optical reading device. The method can be achieved by: determining a first glucose concentration by measuring a first reflectance at about a first wavelength proximate a surface of the test strip having a membrane impregnated with a color-producing reagent; measuring a temperature and a second reflectance at about a second wavelength; determining a second glucose concentration based on the temperature measurement and the second reflectance made at about the second wavelength with an equation of the form:

$$G2=a1*G1+a2*T+a3*K/S_{\lambda 2}+a4*G1*T+a5*G1*K/S_{\lambda 2}+a6*T*K/S_{\lambda 2}+a7*(G1)^2+a8*(T)^2+a9*(K/S_{\lambda 2})^2$$

where:

G2 is the second glucose concentration corrected for temperature and hematocrit effects;

G1 is the first glucose concentration and is determined from the first reflectance measured at about a first wavelength, $\lambda 1$;

T is temperature;

$K/S_{\lambda 2}$ is determined with an equation of the form:

$$K/S_{\lambda 2}=(1-R_2)^2/(2*R_2)$$

where:

$R_2$ is the second reflectance at about the second wavelength, $\lambda 2$, taken at an endpoint time; and Coefficients a1 through a6 depend on the endpoint time at which the first reflectance at first wavelength, $\lambda 1$, is measured; and displaying the second glucose concentration.

In another embodiment, a method of correcting a glucose concentration in a glucose measurement system. The system includes a test strip and an optical reading device. The method can be achieved by: determining a first glucose concentration by measuring a first reflectance at about a first wavelength at a surface of the test strip having a membrane impregnated with a color-producing reagent; measuring a temperature and a second reflectance at about a second wavelength; determining a second glucose concentration based on the second reflectance at about the second wavelength and the measured temperature with the equation of the form:

$$G2=a0+a1*G1+a2*T+a3*K/S_{\lambda 2}+a4*G1*K/S_{\lambda 2}+a5*G1*T$$

where:

G2 is the second glucose concentration corrected for temperature and hematocrit effects;

G1 is the first glucose concentration and is determined from the reflectance measured at about a first wavelength, $\lambda 1$;

T is temperature;

$K/S_{\lambda 2}$ comprises a value obtained with an equation of the form:

$$K/S_{\lambda 2}=(1-R_2)^2/(2*R_2)$$

where:

$R_2$ is the second reflectance at about the second wavelength, $\lambda 2$, taken at an endpoint time; and Coefficients a0 through a5 depend on the endpoint time at which the first reflectance at first wavelength, $\lambda 1$, is measured; and displaying the second glucose concentration.

These and other embodiments, features and advantages will become apparent to those skilled in the art when taken with reference to the following more detailed description of the embodiments of the invention in conjunction with the accompanying drawings that are first briefly described here below.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host", "user", and "subject" refer to any human or animal subject and are not intended to limit the systems or methods to human use, although use of the subject invention in a human patient represents a preferred embodiment.

Figure 1:
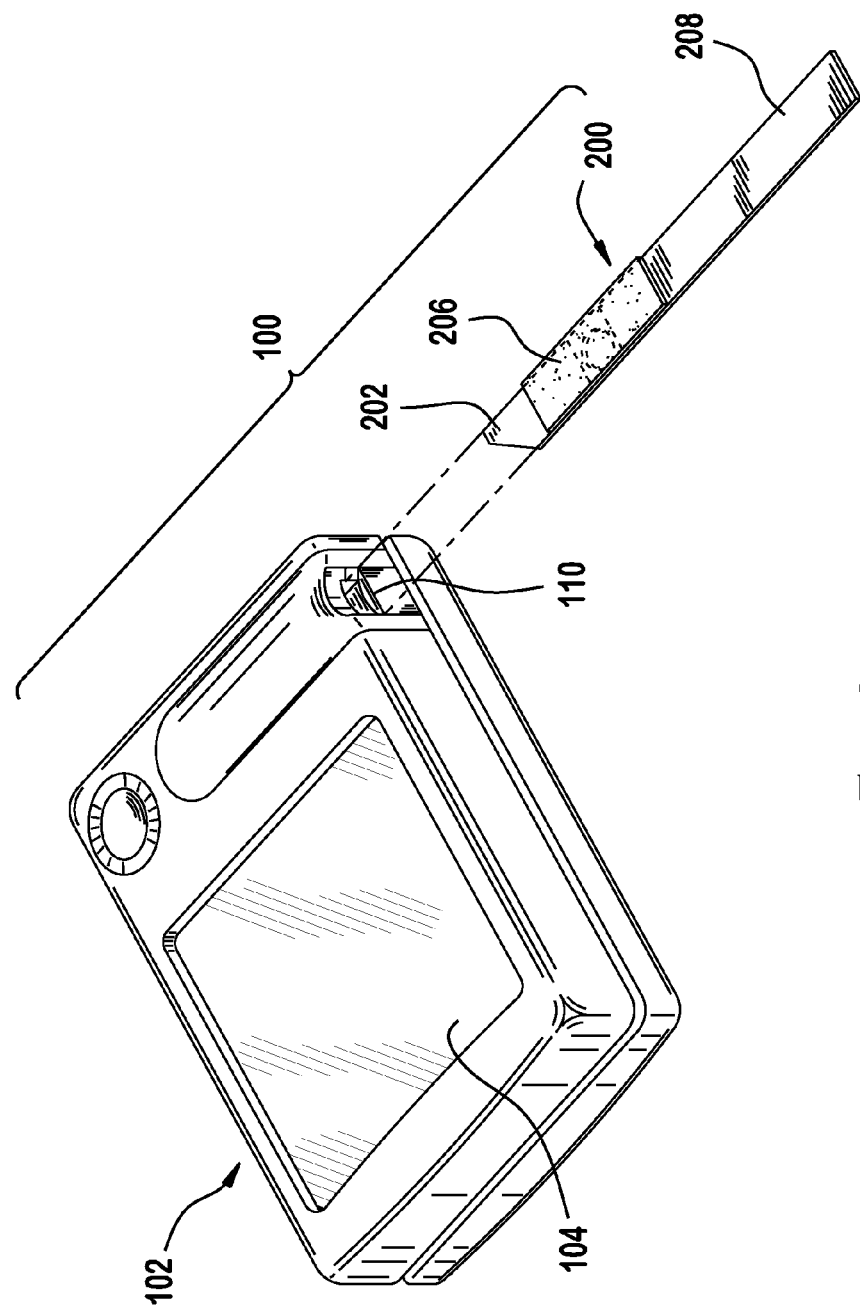
FIG. 1 illustrates an exemplary embodiment of a top perspective view of a system for measuring an analyte including a meter and a test strip.

FIG. 1 illustrates a system 100 for measuring glucose in which the system 100 includes a meter 102 and a test strip 200. One example of the system 100 may be the ONE-TOUCH® SURESTEP® meter and test strip available from LifeScan, Inc. (Milpitas, Calif., U.S.A.). The meter 102 includes a display 104 and a strip port 110. The display 104 may be configured to output a glucose concentration and to show a user interface for prompting a user on how to perform a test. The strip port 110 may be configured to receive a proximal portion 202 of test strip 200 after blood is dosed thereon.

Figure 2A:
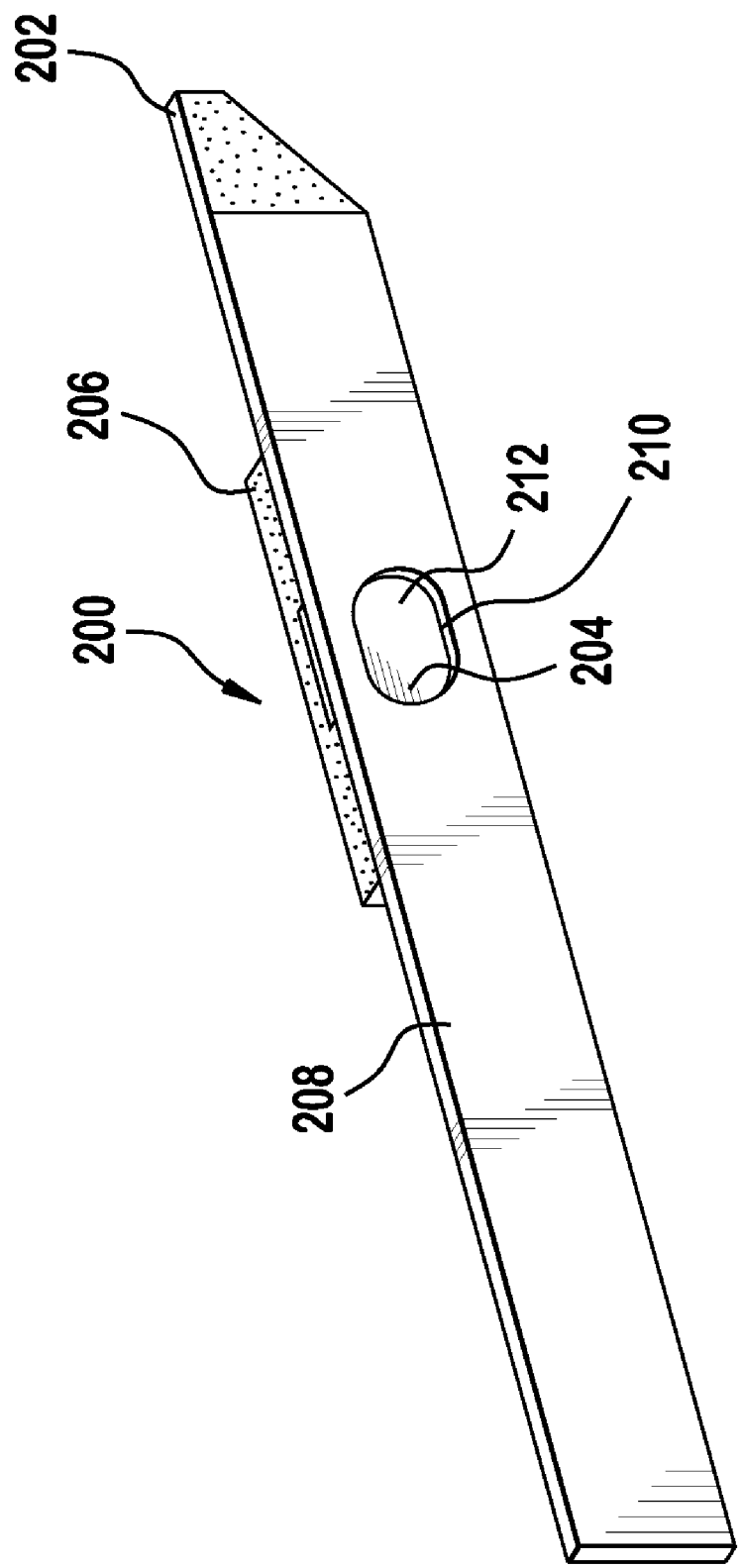
FIG. 2A illustrates an exemplary embodiment of a bottom perspective view of a test strip shown in FIG. 1.
Figure 2B:
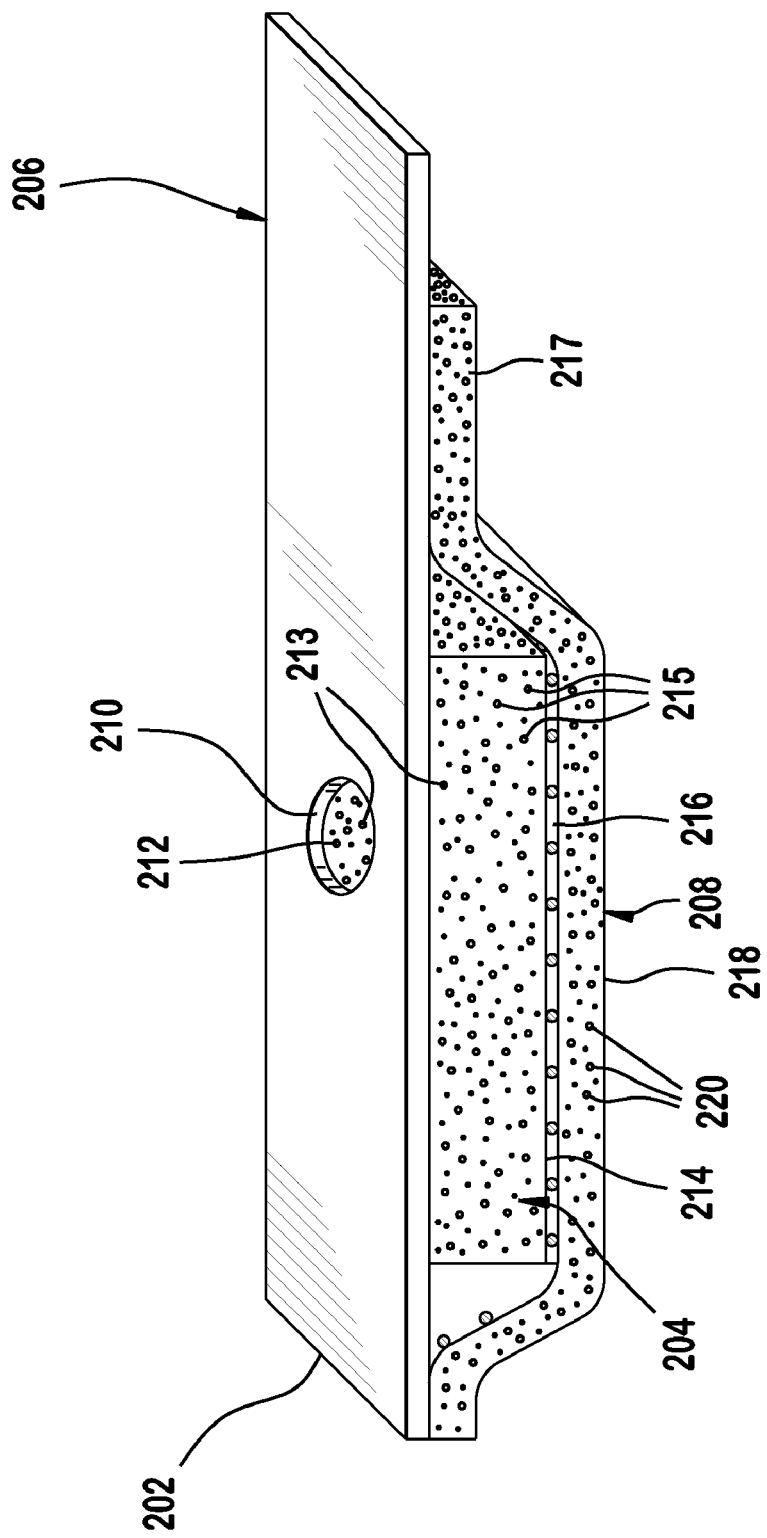
FIG. 2B is an exemplary embodiment of an expanded bottom perspective view of a proximal portion of the test strip that illustrates a plurality of layers in accordance with FIG. 1.

Referring to FIGS. 2A and 2B, the test strip 200 includes a pad 204 sandwiched between a support 206 and a transport medium 208. Support 206 includes an aperture 210 through which a signal may be measured from a testing surface 212 of pad 204. Support 206 may be formed from a material having the property of being sufficiently rigid to be inserted into meter 102 without undue bending or kinking. In one embodiment, support 206 may be formed of materials such as polyolefins (e.g., polyethylene or polypropylene), polystyrene or polyesters. More specifically, support 206 may be formed from white polyester sold by DuPont under the trademark Melinex 329.

Referring back to FIG. 2B, pad 204 may be attached to support 206 such that pad 204 overlaps aperture 210. Pad 204 may be a substantially planar rectangle having a testing surface 212 and an opposing sample receiving surface 214. In an embodiment, testing surface 212 may be attached to support 206 with adhesive (not shown) formed of acrylic, rubber and/or ethylene vinyl acetate. The sample receiving surface 214 may be attached to transport medium 208. Pad 204 may be formed from an anisotropic membrane having a testing surface 212 with relatively small pores 213 and a sample receiving surface 214 having relatively large pores 215. In an embodiment, the small pores 213 may range in diameter from about 0.1 microns to about 1.0 microns and the large pores 215 may range in diameter from about 5 microns to about 50 microns. In general, the pore size progressively increases in size when moving from sample receiving surface 214 to testing surface 212.

Pad 204 may be impregnated with a color forming reagent specific to glucose by, for example, dipping the pad in the color forming reagent in one or more steps after which the pad may be dried. The reagent includes a first and second enzyme and a dye couple. The first enzyme selectively catalyzes a primary reaction with glucose. A product of the primary reaction may be an intermediate that participates in a secondary enzyme-catalyzed reaction that, directly or indirectly, causes a final dye to change color that may be detectable at the testing surface 212 of pad 204. In one embodiment, the reagent includes glucose oxidase, horseradish peroxidase and a dye couple that may be a derivative of MBTH, meta [3-methyl 2-benzothiazolinone hydrozone] N-sulfonyl benzenesulfonate monosodium, coupled with ANS (or 8-anilino 1-naphthalenesulfonate). Glucose oxidase catalyzes the oxidation of glucose to gluconolactone and the concomitant formation of hydrogen peroxide. Horseradish peroxidase then catalyzes the oxidation of the dye couple by hydrogen peroxide. The oxidation of the dye couple results in the formation of a blue color that may be detectable at the testing surface 212 of the pad 204.

An adhesive layer 216 attaches sample receiving surface 214 of pad 204 to transport medium 208 in such a manner that the central portion of sample receiving surface 214 may be unobstructed. In embodiment, adhesive layer may be formed of acrylic, rubber and/or ethylene vinyl acetate. In another embodiment, a hot melt adhesive may be placed in continuous stripes located only near the perimeter of pad 204, leaving a central portion of sample receiving surface 214 of pad 204 substantially unobstructed. In yet another embodiment, transport medium 208 may be formed of a material that fuses to pad 204 with the application of heat and/or pressure.

In an embodiment, transport medium 208 extends past one or more ends of pad 204 so as to form a reservoir 217 for holding excess amounts of blood sample. Transport medium 208 may have a special property of being able to hold excess amounts of blood while the same time being able to transfer a suitable amount of liquid to sample receiving surface 214 through capillary action. Further, transport medium 208 does not readily transfer blood back to the user if a user touches an outer surface 218 of transport medium 208 that contains blood.

To determine the blood glucose concentration, a sample of whole blood is applied to an outer surface 218 of transport medium 208, which includes pores 220 that drain the sample therethrough by capillary action. In one embodiment, the transport medium 208 may be formed from a sintered plastic material such as porous polyethylene materials available from the Porex Corp. of Fairburn, Ga., USA.

The blood sample passes through transport medium 208 and enters pad 204 through sample receiving surface 214 having large pores. The blood then travels toward testing surface 212 that has small pores. As the blood passes through pad 204, the red blood cells become trapped and the glucose-containing plasma passes through. As the sample passes through pad 204, glucose in the sample reacts with the reagent impregnated within pad 204 to form a light-absorbing color on testing surface 212. Unabsorbed light is reflected and may be measured with a light detector 306 (shown in FIG. 3).

Figure 3:
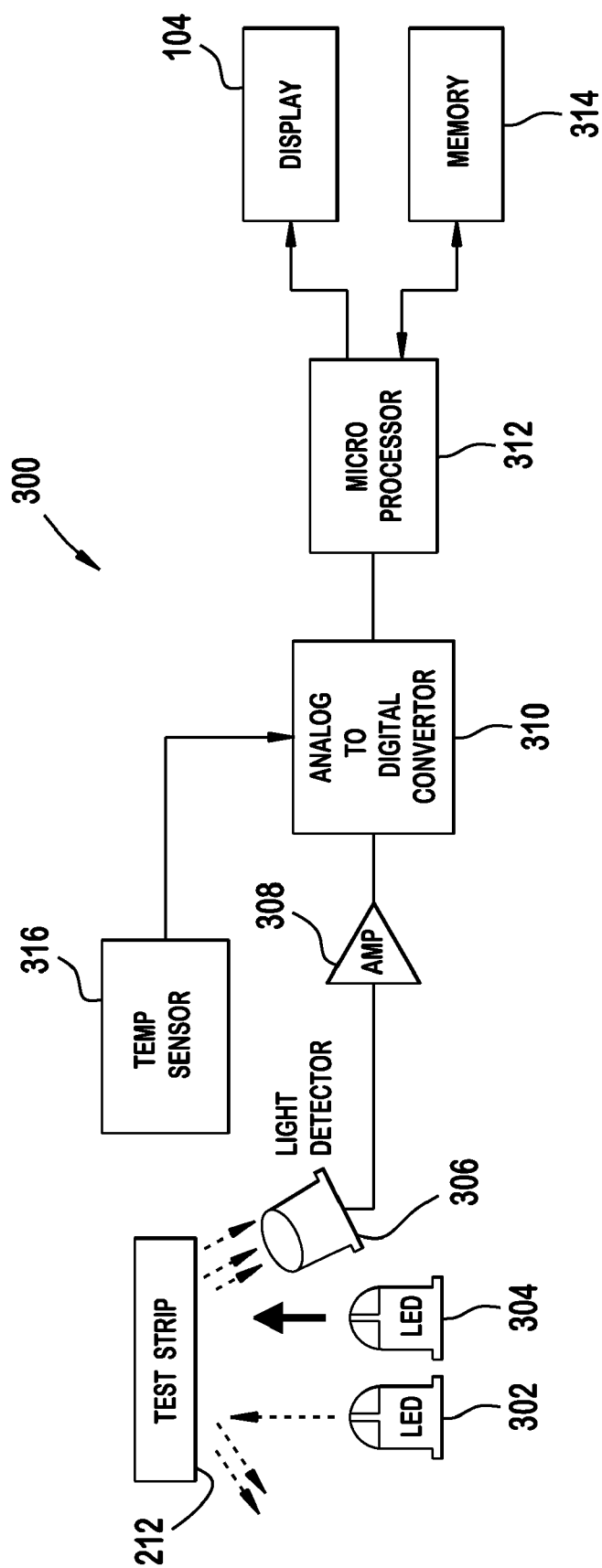
FIG. 3 illustrates an exemplary embodiment of a simplified schematic of the functional components of the system shown in FIG. 1.

FIG. 3 is a simplified schematic of the functional components of the system which illustrates the optical pathway with respect to the pad 204 of the test strip 200. At least one light source, e.g., a light-emitting diode (LED), may be directed at testing surface 212 of pad 204. The at least one light source may be configured to emit light in a range of wavelengths. In the embodiment illustrated in FIG. 3, meter 102 includes a first light source 302 and a second light source 304. First light source 302 may emit radiation at about a first wavelength ranging from about 600 nanometers (nm) to about 700 nm. Second light source 304 may emit radiation at about a second wavelength ranging from about 800 nm to about 1100 nm. In one embodiment, the first light source 302 and the second light source 304 emit radiation at a maximum of about 660 nm and about 940 nm, respectively.

The light reflected from testing surface 212 at first and second wavelengths may be detected by a light detector 306. For each wavelength, the current generated by light detector 306 may be passed to an amplifier 308 (amp), which converts the current to voltage. The voltage from the amplifier 308 may be then fed to an analog-to-digital converter 310. The analogto-digital converter 310 converts the analog voltage from the amplifier 308 to a twelve-bit binary digital number upon command of a microprocessor 312. The digital number thus obtained is proportional to the reflectance at the first and second wavelengths. The reflectance data may be stored in a memory 314 and/or be used to calculate a glucose concentration which may then be displayed on the display 104.

The reflectance values measured at about the first wavelength, e.g., about 660 nm, may be used to determine the glucose concentration in a whole blood sample. As a result of the interaction of the reagent in the test strip 200 with glucose in whole blood, a light-absorbing color may be formed. As the reaction progresses, more color may be formed, and the light reflected to the light detector 306 decreases. The reflectance at about the first wavelength reaches a sufficiently low rate of increase of K/S value at a level proportional to the glucose concentration in the sample. If a stable endpoint value is not achieved after a predetermined time period, e.g., about 2 minutes, then an error warning appears. To determine an endpoint value, the reflectance at about the first wavelength may be measured at about one second intervals and may be converted to K/S (see equation 1 discussed in paragraph 43 below). When m points (typically 6) have been collected, the first and last points are used to compute the percent change of K/S in the m point interval. The first and last points are then shifted by n seconds (typically one second), and the computations are repeated. This process may be repeated until an endpoint condition is detected.

If a certain number (typically 3) of consecutive percent change values of K/S are positive and all less than a certain amount (typically 1%), then it is determined that the observation of the reaction sequence started before endpoint A (see FIG. 5) and endpoint A has now been reached.

If a certain number (typically 3) of consecutive percent change values of K/S are negative and all greater than a certain amount (typically −1%), then it is determined that the observation of the reaction sequence started after endpoint B (see FIG. 5) and endpoint B has now been reached.

The reflectance values measured at about the second wavelength, e.g., about 940 nm, may be used to determine whether enough blood has been applied to the test strip 200 and to measure the amount of hemoglobin. Hemoglobin in red blood cells absorbs light at about the second wavelength. Note that the hematocrit value may be directly proportional to the amount of hemoglobin. Thus, when whole blood is applied to the test strip 200, light reflected at about the second wavelength decreases, which can be measured at detector 306.

If insufficient sample has been applied to the test strip 200, then a smaller change in reflected light may be detected at about the second wavelength, and an error warning informs the user that not enough blood was applied to the test strip 200. Note that a typical blood sample having a low hemoglobin content that may be dosed onto the test strip will still cause a greater decrease in reflectance than a partially filled tested strip. Thus, the second wavelength can be effective for both monitoring whether the test strip is sufficiently filled with blood and for measuring the amount of hemoglobin.

For most situations, applicant believes that the first glucose concentration may be a sufficiently accurate measurement of blood glucose for people with diabetes. However, under certain circumstances, where the blood sample may have an extreme hematocrit (e.g. 20% or 70%) and/or be tested under an extreme temperature conditions (e.g., about 10° C. or less, or about 45° C. or more), applicant believes that there is a need to calculate a second glucose concentration, which is more accurate than the first glucose concentration. Applicants have determined that the reflectance values measured at about the second wavelength may be used to reduce the effect of the hematocrit level and temperature on the glucose measurement. However, applicants also found the reflectance signal at about the second wavelength (e.g., about 940 nm) was lower by at least an order of magnitude than the reflectance signal at about the first wavelength (e.g., about 660 nm). Applicants also found that the background noise in measuring the second reflectance was substantially higher than for the first reflectance. Thus, applicants were surprised that a more accurate second glucose measurement could be calculated using the second wavelength without degrading the precision of the measurement.

The hematocrit level represents a percentage of the volume of a whole blood sample occupied by red blood cells. More red blood cells are present at higher hematocrit levels, resulting in greater amounts of hemoglobin which absorbs light at about the second wavelength, e.g., about 940 nm. Thus, as the hematocrit level increases, less reflected light at about the second wavelength may be detected by the light detector 306. Since reflectance at about the second wavelength may be directly related to the hematocrit level, the reflectance at about the second wavelength may be used to correct the glucose concentration calculated from the reflectance at about the first wavelength, e.g., about 660 nm, as will be described in more detail below. The amount of light absorbed and, consequently, reflected at about the second wavelength may be small. Studies of the absorption spectra of hemoglobin indicate that the signal in the region of about 940 nm may be about ten times less than that at about 660 nm (see Horecker, B L, *Absorption Spectra of Hemoglobin and its Derivatives in the Visible and Near IR Regions*, J. of Biological Chemistry, Vol. 148, 173-183 [1943], which is incorporated by reference as set forth herein).

Referring again to FIG. 3, meter 102 also includes a temperature sensor 316 for measuring ambient temperature. An exemplary temperature sensor may include a thermocouple or a thermistor. The temperature sensor 316 typically may be placed in close proximity to the test strip 200 such that the measured temperature may be representative of the conditions at proximate the surface of the pad 204. The voltage output from the temperature sensor 316 may be fed to the analog-to-digital converter which converts the analog voltage to a twelve-bit binary digital number upon command of the microprocessor 312. The digital number thus obtained is proportional to the temperature at the time of the test. The temperature data may be stored in memory 314 and/or be used to determine how long the reaction between the reagent and glucose in blood should be allowed to proceed before declaring an error if an endpoint is not reached. Briefly, the determination of an analyte concentration such as glucose depends upon a chemical reaction occurring within the pad 204 of the test strip 200. The rate of reaction of the chemical reaction going to completion will be a function of temperature. Thus, if the temperature may be too low or too high, e.g., less than about 10° C. or greater than 40° C., then the meter 102 will report an error. If the temperature is low but still operable, then the meter 102 will adjust for the low temperature by extending the reading time of the reaction zone. The meter determines how long to extend the reading time based on a lookup table of time limits versus temperature. The time limits are empirically determined to be the normal upper limits of reaction time with typical test strip lots. Applicants have found that the ambient temperature measured by the meter may also be used to improve the accuracy of the glucose concentration, as will be described in more detail below.

Figure 4:
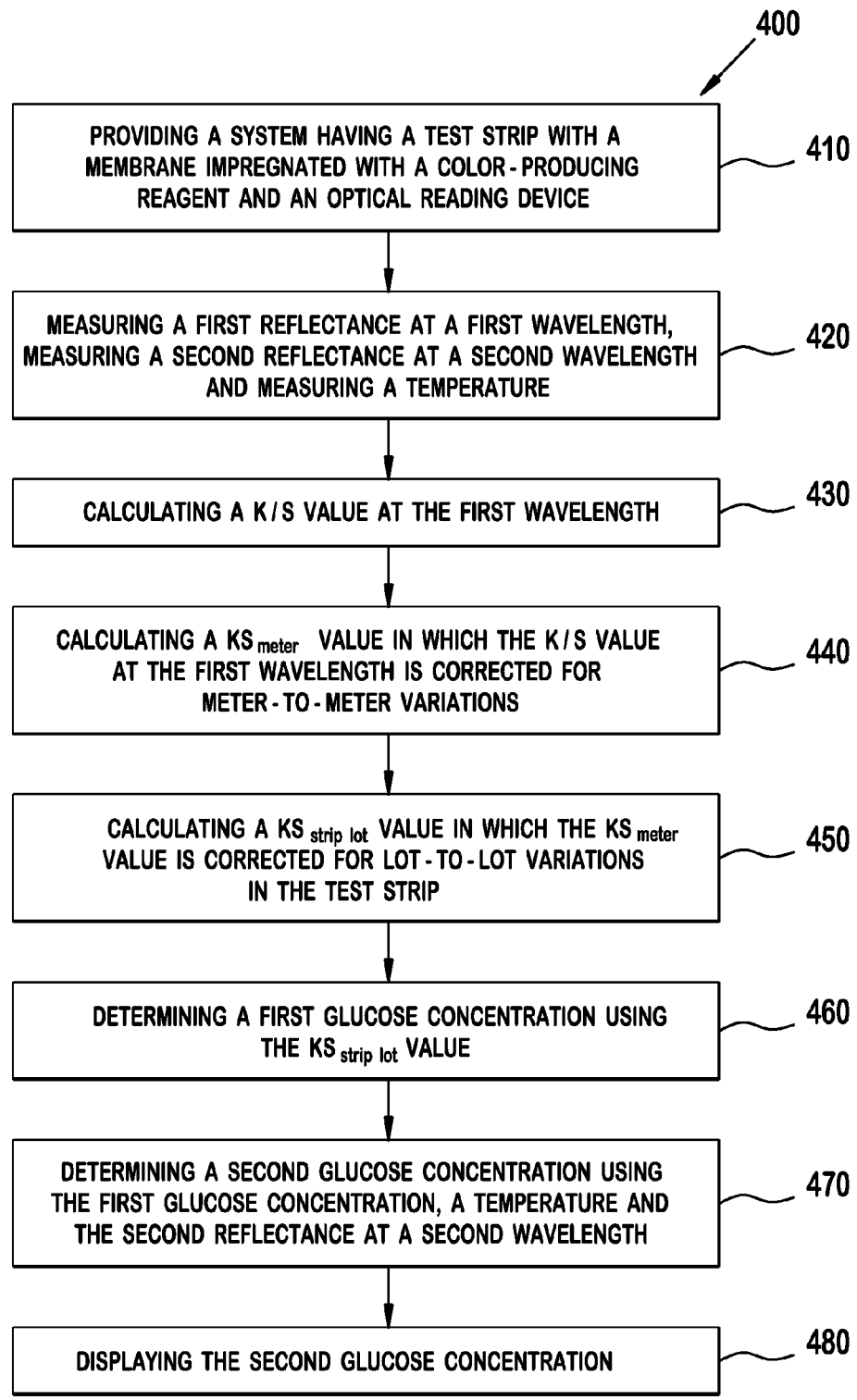
FIG. 4 illustrates an exemplary embodiment of a flow chart of a method of applying a temperature and hematocrit correction to a method of calculating a glucose concentration using the system shown in FIG. 1.

Referring to FIG. 4, the aforementioned meter 102 and test strip 200 embodiments may be configured to carry out method 400 to apply a temperature and hematocrit correction to a glucose concentration that about uses will now be described.

In exemplary step 410, meter 102 and test strip 200 are provided. Meter 102 includes optical components that can be used to direct light to testing surface 212 of test strip 200 and to detect reflected light from testing surface 212 of test strip 200. Meter 102 also includes microprocessor 312 with an algorithm for the method of determining a corrected glucose concentration in a whole blood sample as disclosed herein.

In exemplary step 420, a first glucose concentration may be determined by measuring a first reflectance at about a first wavelength, e.g., about 660 nm, proximate a surface of test strip 200 having pad 204 impregnated with a color-producing reagent. A second reflectance at about a second wavelength, e.g., about 940 nm, is then measured at proximate the surface of test strip 200 and a temperature may be measured near test strip 200 with temperature sensor 316. In exemplary step 430, the first reflectance is mathematically transformed to a $K/S_{\lambda 1}$ value using the Kubelka-Monk equation (Equation 1). In general, a K/S value may be preferred over the use of a reflectance value because the K/S value will have a proportional relationship that increases with the analyte concentration.

$$K/S_{\lambda 1} = \frac{(1-R_1)^2}{2R_1} \quad (1)$$

where:
$K/S_{\lambda 1}$ is the K/S value at about the first wavelength, $\lambda 1$, at which the first reflectance is measured. $\lambda 1$ may have units of, for example, nm; and $R_1$ is the first reflectance measured taken at an endpoint time.

In exemplary step 440, the $K/S_{\lambda 1}$ value, obtained from Equation 1, is next corrected for meter-to-meter variations using the following equation:

$$KS_{meter} = a0 + a1*(K/S_{\lambda 1}) \quad (2)$$

where:
$KS_{meter}$ is the $K/S_{\lambda 1}$ value corrected for meter-to-meter variations; and
a0 and a1 are coefficients saved to the memory for each meter when calibrated at the factory.

Note that meter-to-meter variations can arise due to variability in LED 302.

The $KS_{meter}$ value obtained from Equation 2 is then corrected for lot-to-lot strip variations in exemplary step 450. Each lot of strips has been tested at the factory and given a single code number. The code number references a set of coefficients, e.g., 21 sets, stored in the memory of each meter and indexed against a code number. For example, a linear correlation is believed adequate to account for lot-to-lot variations in the strip in the glucose test and, hence, two coefficients per set are stored against each code number. Upon inserting a strip into the meter 102, the user will be asked to enter the proper code number found on the package of strips being employed. The microprocessor will then obtain the proper coefficients from a look-up table. To correct the $KS_{meter}$ value for lot-to-lot strip variations, the following equation may be used:

$$KS_{strip\ lot} = b0 + b1*(KS_{meter}) \quad (3)$$

where:
$KS_{strip\ lot}$ is the $KS_{meter}$ value corrected for lot-to-lot strip variations; and b0 and b1 are coefficients provided in a look-up table in the microprocessor.

Next, in exemplary step 460, a first glucose concentration is calculated using the following equation:

$$G1 = c0 + c1*KS_{strip\ lot} + C2*(KSstrip_{lot})^2 + C3*(KSstrip_{lot})^3 \quad (4)$$

where:
G1 is the first glucose concentration in, for example, mg/dL or mmole/L; and
c0-c3 are empirically derived constants which may be stored in a look-up table in the microprocessor.

The first glucose concentration is then corrected for temperature and hematocrit effects in the next exemplary step 470. In embodiments in which "off-meter" dosing may be used, i.e., the sample is applied to the test strip 200 prior to insertion into the meter 102, the reflectance at about the first wavelength may be measured at any time up to a specified time limit such as, for example, about 2 minutes. Note that "off meter" dosing differs from "on-meter" dosing where the test strip must be physically attached to the meter before sample is applied. In general, a user can more easily dose a hanging drop of blood on a fingertip to a test strip that is not attached to a meter. An unattached test strip is easier to maneuver than a test strip physically tethered to a meter. Also, in environments where multiple users are tested with one meter, the potential for contamination is lower. It should be noted that the amount of time that passes before a user inserts a test strip into the meter can vary when performing an "off-meter" dosing. Surprisingly, applicants have found that variations in the strip insertion timing do not have an effect on accuracy when performed with a specified time limit of less than about two minutes.

Figure 5:
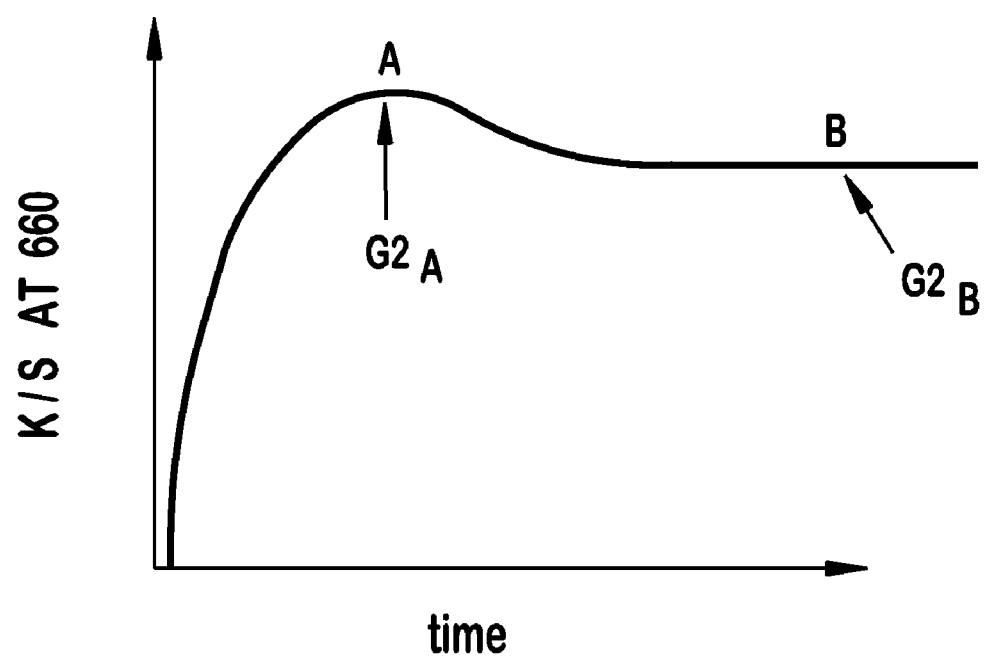
FIG. 5 illustrates an exemplary embodiment of a graph showing K/S at about a first wavelength as a function of time.

As illustrated in FIG. 5, the applicants have observed that the $K/S_{\lambda 1}$ may reach a maximum value and then may drift down over time to a stable value. The time required to reach the maximum value can depend on the reaction rate and amount of glucose in the sample. A stable value may refer to a situation where the K/S value does not change substantially with time. In an embodiment, the stable value may also be referred to as constant or plateau region. Referring back to FIG. 5, the maximum value region is denoted by an "A" and the stable value region may be denoted by "B." An "endpoint time" reflectance can be used to calculate the $K/S_{\lambda 1}$ in equation 1. The endpoint time K/S can be based on the maximum value (A) or the stable value (B). Note that there is believed to be an advantage in using region "A" because the test time can be shorter.

In contrast to $K/S_{\lambda 1}$, $K/S_{\lambda 2}$ may approach a stable value rapidly with time (not shown). Note that the $K/S_{\lambda 2}$ depends on the amount of hemoglobin in the sample and does not depend on the rate of subsequent enzymatic reaction once the strip is dosed with blood. Thus, once pad 204 is fully wetted with blood, the $K/S_{\lambda 2}$ may be a stable value that does not change with time. In an embodiment, $K/S_{\lambda 2}$ may be monitored substantially concurrently or substantially at the same time as $K/S_{\lambda 1}$. In another embodiment, $K/S_{\lambda 2}$ may be monitored at a different time as $K/S_{\lambda 1}$. For example, an optical chopper or alternating pulses of the LED's may be used to alternate the illumination of testing surface 212 between LED 302 and LED 304.

Thus, the equation for a second glucose concentration that may be empirically derived to correct for temperature and hematocrit effects depends on the time at which the reflectance at about the first wavelength is taken. For example, the equation derived will be different (i.e., will have different coefficients) at region A and at region B, as illustrated in FIG. 5. In general, the derived equation may be of the form:

$$G2 = \sum_{i=0}^{\infty} \sum_{j=0}^{\infty} \sum_{k=0}^{\infty} \alpha_{(i,j,k)} K/S_{\lambda 2}{}^{i} * T^{j} * G1^{k} \quad (5)$$

where:

G2 is the second glucose concentration corrected for temperature and hematocrit effects. G2 may have units of, for example, mg/dL or mmoles/L;

T is temperature in, for example, degrees Celsius or Kelvin; and $K/S_{\lambda 2}$ is determined with an equation of the form:

$$K/S_{\lambda 2} = (1-R_2)^2/(2*R_2)$$

where:

$R_2$ is the second reflectance at about the second wavelength, λ2, taken at an endpoint time; and i, j, and k are integers ranging from zero to infinity.

In embodiments, i, j, or k may range from zero to 3 but may not be set to three at the same time. In an embodiment, Equation (5) becomes a polynomial equation of the form:

$$\begin{aligned}G2 = {} & a0 + a1*G1 + a2*T + a3*K/S_{\lambda 2} + a4*G1*T + \\ & a5*G1*K/S_{\lambda 2} + a6*T*K/S_{22} + a7*(G1)^2 + a8*(T)^2 + \\ & a9*(K/S_{\lambda 2})^2 + a10*(G1)^3 + a11*(T)^3 + a12*(K/\\ & S_{\lambda 2})^3 + a13*G1*T*K/S_{22} + a14*(G1)^2*T + a15* \\ & (G1)^2*(K/S_{\lambda 2}) + a16*G1*T^2 + a17*G1*(K/S_{\lambda 2})^2 + \\ & a18*T*(K/S_{\lambda 2})^2 + a19*T^2*(K/S_{\lambda 2}) \end{aligned} \quad (6)$$

where:

G2 is the second glucose concentration corrected for temperature and hematocrit effects. G2 may have units of, for example, mg/dL or mmoles/L;

T is temperature in, for example, degrees Celsius or Kelvin; and $K/S_{\lambda 2}$ is determined with an equation of the form:

$$K/S_{\lambda 2} = (1-R_2)^2/(2*R_2)$$

where:

$R_2$ is the second reflectance at about the second wavelength, λ2, taken at an endpoint time in, for example, seconds; and Coefficients a0 through a19 depend on the endpoint time at which the reflectance at about the first wavelength, λ1, is measured.

In an embodiment of equation (6) in which coefficients a10 through a19 were determined to be substantially less than coefficients a1 to a9, and were therefore set to zero, Equation (6) becomes a polynomial equation of the form:

$$\begin{aligned}G2 = {} & a0 + a1*G1 + a2*T + a3*K/S_{\lambda 2} + a4*G1*T + \\ & a5*G1*K/S_{\lambda 2} + a6*T*K/S_{\lambda 2} + a7*(G1)^2 + a8*(T)^2 + \\ & a9*(K/S_{\lambda 2})^2 \end{aligned} \quad (7)$$

In an embodiment of equation (6) in which coefficients a7 through a19 were determined to be substantially less than coefficients a1 to a6, and were therefore set to zero, Equation (6) becomes a linear equation of the form:

$$\begin{aligned}G2 = {} & a0 + a1*G1 + a2*T + a3*K/S_{\lambda 2} + a4*G1*T + \\ & a5*G1*K/S_{\lambda 2} + a6*T*K/S_{\lambda 2} \end{aligned} \quad (8)$$

In an embodiment of equation (5) in which G1 is corrected for only hematocrit effects, all the terms in Equation (5) that include T will be zero such that Equation (6) has the form:

$$G2 = \sum_{i=0}^{\infty} \sum_{j=0}^{\infty} \alpha_{(i,j)} K/S_{\lambda 2}{}^{i} * G1^{j} \quad (9)$$

In the last exemplary step 480, the second (and final) glucose concentration, G2, may be displayed on the meter 102. Because temperature and hematocrit effects are taken into account, G2 is a more accurate test result.

Example 1

Determination of G1 Corrected for Temperature and Hematocrit Effects Using a Polynomial Equation to Fit the Data First glucose concentration, G1, data was obtained for about thirty lots of test strips by testing each lot with whole blood containing glucose at about 100-350 mg/dL and having hematocrit values of 24-60%. Each lot of test strips was also tested at temperatures ranging from about 24° C.-about 35° C. One test strip at each condition of glucose, hematocrit and temperature was tested for each lot of test strips. Referring again to FIG. 5, G1 was determined at the maximum value for K/S at about 660 nm (i.e., at region A) and at a stable value for reflectance at about 660 nm (i.e., at region B). G2, the second glucose concentration corrected for temperature and hematocrit, was then determined by using the following polynomial equation:

$$\begin{aligned}G2 = {} & a0 + a1*(G1) - a2*T + a3*(K/S_{\lambda 2}) + a7*(G1)^2 + \\ & a8*T^2 + a9*(K/S_{\lambda 2})^2 \end{aligned} \quad (10)$$

Equation 10 is based on equation 6 in which coefficients a4 to a6, and a10 to a19 were determined to be substantially less than coefficients a1 to a3, and a7 to a9, and were therefore set to zero.

At the maximum value for K/S at about 660 nm (i.e., at region A in FIG. 5), the Equation 10 is:

$$\begin{aligned}G2_A = {} & -30.9 + 1.37(G1) - 5.94T + 1527(K/S_{\lambda 2}) - 0.000652 \\ & (G1)^2 + 0.122T^2 + 2521(K/S_{\lambda 2})^2 \end{aligned} \quad (11)$$

At the stable value for K/S at about 660 nm (i.e., at region B in FIG. 5), the Equation 10 is:

$$\begin{aligned}G2_B = {} & -293 + 1.96(G1) + 8.67T + 817(K/S_{\lambda 2}) - 0.00198 \\ & (G1)^2 - 0.0761T^2 + 7352(K/S_{\lambda 2})^2 \end{aligned} \quad (12)$$

Figure 6A:
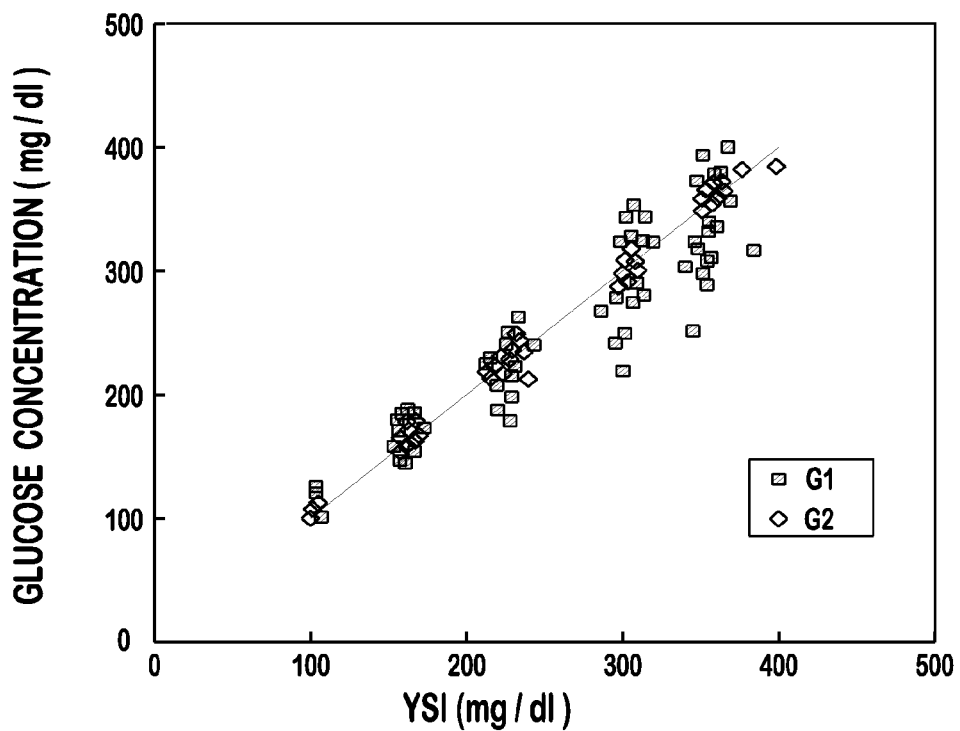
FIG. 6A illustrates an exemplary embodiment of a graph correlating the first and second glucose concentrations to a reference glucose concentration. The second glucose concentration was obtained using a polynomial function and a maximum K/S value at about 660 nanometers, (see region A in FIG. 5)
Figure 6B:
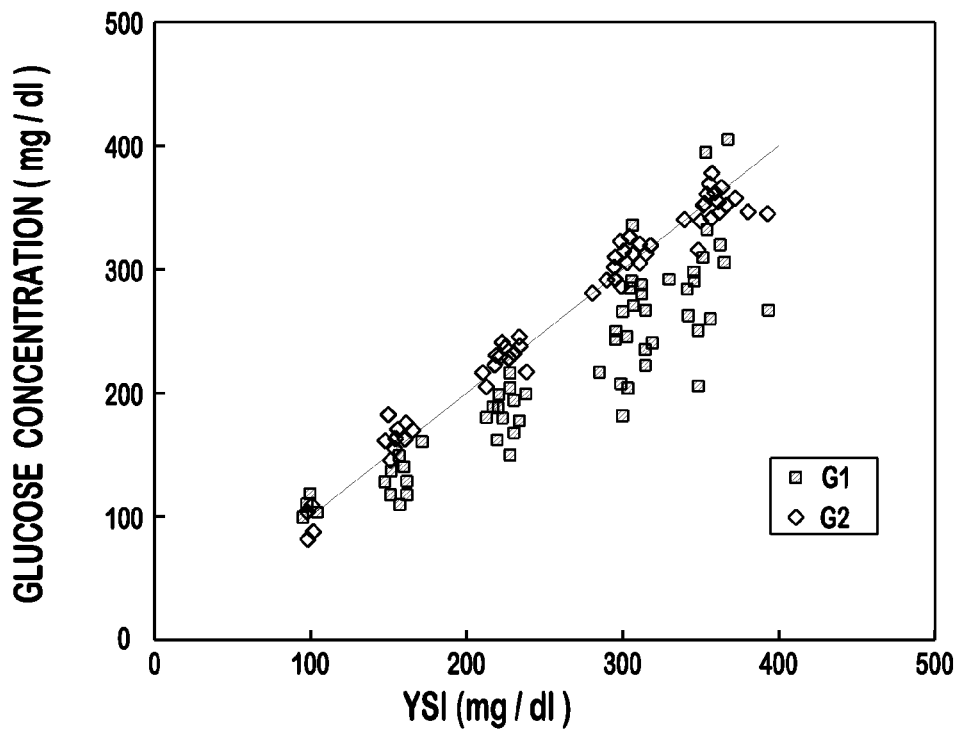
FIG. 6B illustrates an exemplary embodiment of a graph correlating the first and second glucose concentrations to a reference glucose concentration. The second glucose concentration was obtained using a polynomial function and a stable K/S value at about 660 nanometers, (see region B in FIG. 5)

FIG. 6A is a chart illustrating G1 and G2, where G2 was calculated using maximum K/S values at about 660 nm (Region A) with equation 11. Similarly, FIG. 6B is a chart illustrating G1 and G2, where G2 was calculated using stable value K/S at about 660 nm with equation 12. For each set of data, glucose concentration was graphed as a function of a reference glucose concentration obtained by testing the same whole blood samples as described above with a reference instrument, e.g., the YSI 2300 STAT Plus Glucose & Lactate Analyzer (available from YSI Life Sciences, Yellow Springs, Ohio). Regression analysis of each set of data resulted in an output summarized in Tables 1 and 2 below.

TABLE 1

| Summary of regression analysis output for data at the maximum value for K/S at about 660 nm using Equation 11 | | |
|---|---|---|
| Regression Output | G1 | G2 |
| $R^2$ | 0.912 | 0.988 |
| Standard Error of Prediction | 24.3 | 9.53 |

TABLE 2

| Summary of regression analysis output for data at the stable value for reflectance at about 660 nm using Equation 12 | | |
|---|---|---|
| Regression Output | G1 | G2 |
| $R^2$ | 0.849 | 0.982 |
| Standard Error of Prediction | 30.5 | 11.8 |

As illustrated by FIGS. 6A and 6B and Tables 1 and 2, correcting G1 for temperature and hematocrit effects improves $R^2$ and the standard error of prediction, thus improving the accuracy of the second (and final) glucose concentration, G2.

Example 2

Determination of G1 Corrected for Temperature and Hematocrit Effects Using a Linear Equation to Fit the Data The same data sets as were used in Example 1 were also fit to a linear model, resulting in a equation of the form:

$$G2 = a0 + a1*(G1) - a2*T + a4*(G1)*(K/S_{\lambda 2}) + a5*(G1)*T \quad (13)$$

Equation 13 is based on equation 6 in which coefficients a3, and a6 to a19 were determined to be substantially less than coefficients a1, a2, a4, and a5, and were therefore set to zero.

At the maximum value for K/S at about 660 nm (i.e., at region A in FIG. 5), the Equation 13 is:

$$G2_A = 41.8 + 0.396*(G1) - 1.92*T + 7.63*(G1)*(K/S_{\lambda 2}) + 0.0147*(G1)*T \quad (14)$$

At the stable value for K/S at about 660 nm (i.e., at region B in FIG. 5), the Equation 13 is:

$$G2_B = 31.3 - 786*(K/S_{\lambda 2}) + 11.6*(G1)*(K/S_{\lambda 2}) + 0.0259*(G1)*T \quad (15)$$

Note that there are no G1 or T terms in Equation 15 because the coefficients a1 and a2 in Equation 12 are zero.

Figure 7A:
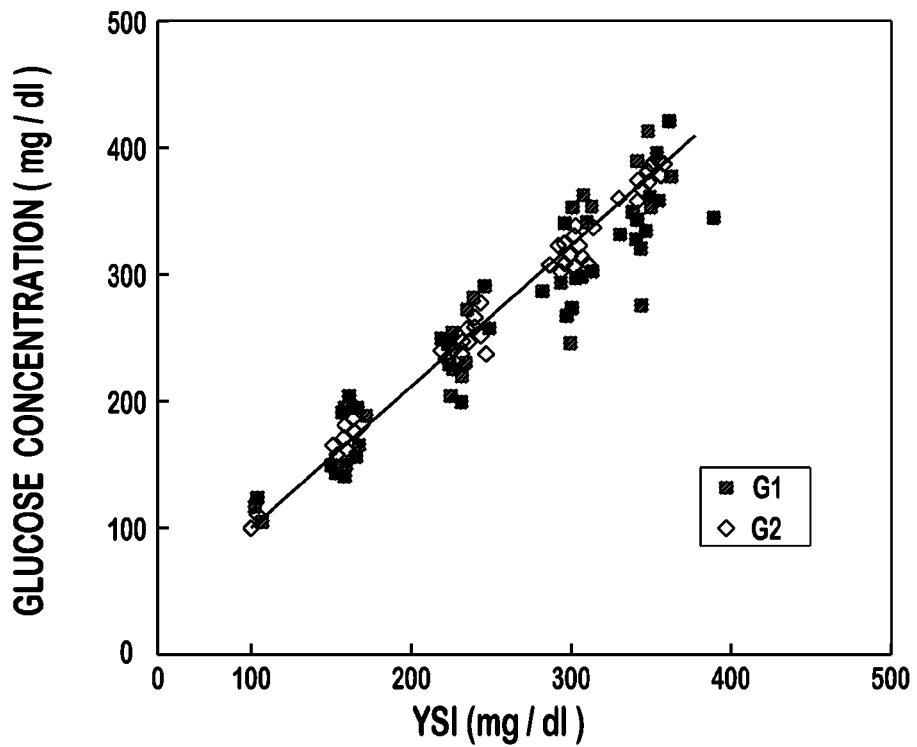
FIG. 7A illustrates an exemplary embodiment of a graph correlating the first and second glucose concentrations to a reference glucose concentration. The second glucose concentration was obtained using a linear function and a maximum K/S value at about 660 nanometers, (see region A in FIG. 5)

FIG. 7A is a chart illustrating G1 and G2, where G2 was calculated using maximum K/S values at about 660 nm (Region A) with equation 14. Similarly, FIG. 6B is a chart illustrating G1 and G2, where G2 was calculated using stable value K/S at about 660 nm with equation 15. For each set of data glucose concentration was graphed as a function of a reference glucose concentration obtained by testing the same whole blood samples as described above with a reference instrument, e.g., the YSI 2300 STAT Plus Glucose & Lactate Analyzer (available from YSI Life Sciences, Yellow Springs, Ohio). Regression analysis of each set of data resulted in an output summarized in Tables 3 and 4 below.

TABLE 3

Summary of regression analysis output for data at the maximum value for K/S at about 660 nm using Equation 14

| Regression Output | G1 | G2 |
| --- | --- | --- |
| $R^2$ | 0.912 | 0.995 |
| Standard Error of Prediction | 24.3 | 6.26 |

TABLE 2

Summary of regression analysis output for data at the stable value for reflectance at about 660 nm using Equation 15

| Regression Output | G1 | G2 |
| --- | --- | --- |
| $R^2$ | 0.849 | 0.987 |
| Standard Error of Prediction | 30.5 | 9.87 |

Figure 7B:
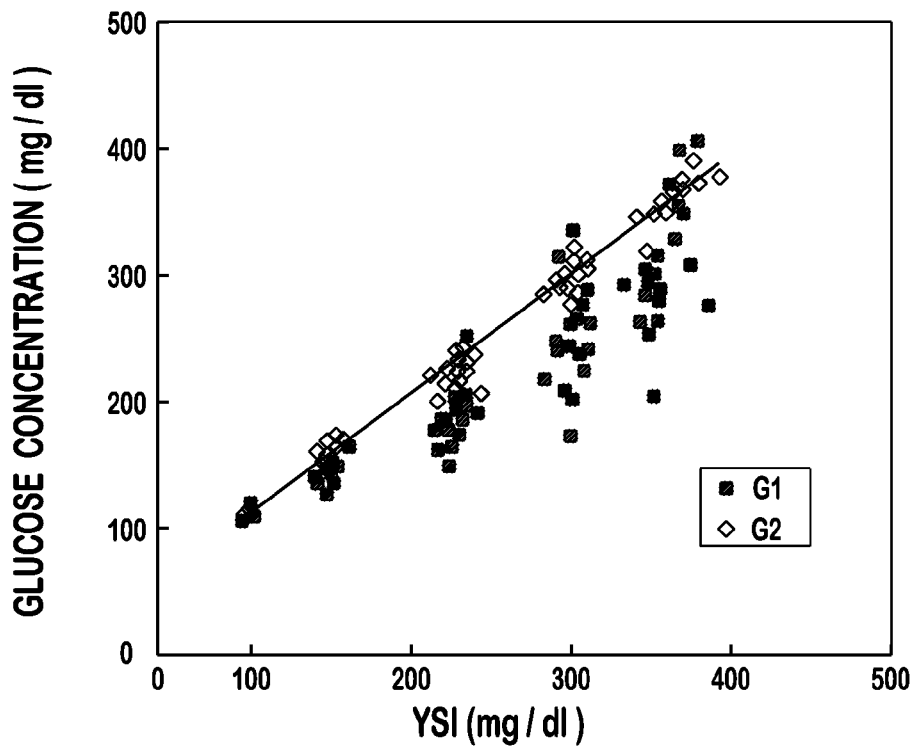
FIG. 7B illustrates an exemplary embodiment of a graph correlating the first and second glucose concentrations to a reference glucose concentration. The second glucose concentration was obtained using a linear function and a stable K/S value at about 660 nanometers, (see region B in FIG. 5).

As illustrated by FIGS. 7A and 7B and Tables 3 and 4, correcting G1 for temperature and hematocrit effects improves $R^2$ and the standard error of prediction, thus improving the accuracy of the second (and final) glucose concentration, G2.

It is noted that the various methods described herein can be used to generate software codes using off-the-shelf software development tools such as, for example, C or C+ (with appropriate compiler and other ancillaries known to those skilled in the art). The methods, additionally, may be transformed into other software language s (such as, for example, Visual Studio 6.0, Windows 2000 Server, and SQL Server 2000) depending on the requirements and the availability of new software languages for coding the methods. Additionally, the various methods described, once transformed into suitable software codes, may be embodied in any computer-readable storage medium that, when executed by a suitable microprocessor or computer, are operable to carry out the steps described in these methods along with any other necessary steps.

In conclusion, the system and methods described and illustrated herein can be used to reduce the effect of hematocrit and temperature on the glucose measurement. Thus, the glucose result obtained with the subject system and method is believed to be more accurate.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of correcting a glucose concentration in a glucose measurement system having a test strip and an optical reading device, the method comprising:
   determining a first glucose concentration by measuring a first reflectance at about a first wavelength proximate a surface of the test strip having a membrane impregnated with a color-producing reagent;
   measuring a temperature and measuring a second reflectance at about a second wavelength;
   determining a second glucose concentration with at least one equation to correct the first glucose concentration with the temperature and the second reflectance at about the second wavelength; and
   displaying the second glucose concentration.

2. The method of claim 1, wherein the at least one equation comprises an equation of the form:

$$G2 = a0 + a1*G1 + a2*T + a3*K/S_{\lambda 2} + a4*(G1)^2 + a5*(T)^2 + a6*(K/S_{\lambda 2})^2$$

where:
G2 is the second glucose concentration corrected for temperature and hematocrit effects;
G1 is the first glucose concentration and is determined from the first reflectance measured at about a first wavelength, $\lambda 1$;
T is temperature;
$K/S_{\lambda 2}$ comprises a value obtained with an equation of the form:

$$K/S_{\lambda 2} = (1 - R_2)^2 / (2*R_2)$$

where:
- $R_2$ is the second reflectance at about the second wavelength, λ2, taken at an endpoint time; and
- Coefficients a0 through a6 depend on the endpoint time at which the first reflectance at about the first wavelength, λ1, is measured.

3. A method of correcting a glucose concentration in a glucose measurement system having a test strip and an optical reading device, the method comprising:
- determining a first glucose concentration by measuring a first reflectance at about a first wavelength proximate a surface of the test strip having a membrane impregnated with a color-producing reagent;
- measuring a temperature and measuring a second reflectance at about a second wavelength;
- determining a second glucose concentration based on the temperature and the second reflectance at about the second wavelength with an equation of the form:

$$G2=a0+a1*G1+a2*T+a3*K/S_{\lambda 2}+a4*G1*T+a5*G1*K/S_{\lambda 2}+a6*T*K/S_{\lambda 2}+a7*(G1)^2+a8*(T)^2+a9*(K/S_{\lambda 2})^2+a10*(G1)^3+a11*(T)^3+a12*(K/S_{\lambda 2})^3+a13*G1*T*K/S_{\lambda 2}+a14*(G1)^2*T+a15*(G1)^2*(K/S_{\lambda 2})+a16*G1*T^2+a17*G1*(K/S_{\lambda 2})^2+a18*T*(K/S_{\lambda 2})^2+a19*T^2*(K/S_{\lambda 2})$$

where:
- G2 is the second glucose concentration corrected for temperature and hematocrit effects;
- G1 is the first glucose concentration and is determined from the reflectance measured at about a first wavelength, λ1;
- T is temperature;
- $K/S_{\lambda 2}$ comprises a value obtained with an equation of the form:

$$K/S_{\lambda 2}=(1-R_2)^2/(2*R_2)$$

where:
- $R_2$ is the second reflectance at about the second wavelength, λ2, taken at an endpoint time; and
- Coefficients a0 through a19 depend on the endpoint time at which the first reflectance at about the first wavelength, λ1, is measured; and
- displaying the second glucose concentration.

4. A method of correcting a glucose concentration in a glucose measurement system having a test strip and an optical reading device, the method comprising:
- determining a first glucose concentration by measuring a first reflectance at about a first wavelength proximate a surface of the test strip having a membrane impregnated with a color-producing reagent;
- measuring a temperature and measuring a second reflectance at about a second wavelength;
- determining a second glucose concentration based on the temperature measurement and the second reflectance made at about the second wavelength with an equation of the form:

$$G2=a1*G1+a2*T+a3*K/S_{\lambda 2}+a4*G1*T+a5*G1*K/S_{\lambda 2}+a6*T*K/S_{\lambda 2}+a7*(G1)^2+a8*(T)^2+a9*(K/S_{\lambda 2})^2$$

where:
- G2 is the second glucose concentration corrected for temperature and hematocrit effects;
- G1 is the first glucose concentration and is determined from the first reflectance measured at about a first wavelength, λ1;
- T is temperature;
- $K/S_{\lambda 2}$ is determined with an equation of the form:

$$K/S_{\lambda 2}=(1-R_2)^2/(2*R_2)$$

where:
- $R_2$ is the second reflectance at about the second wavelength, λ2, taken at an endpoint time; and
- Coefficients a1 through a6 depend on the endpoint time at which the first reflectance at first wavelength, λ1, is measured; and
- displaying the second glucose concentration.

5. A method of correcting a glucose concentration in a glucose measurement system having a test strip and an optical reading device, the method comprising:
- determining a first glucose concentration by measuring a first reflectance at about a first wavelength at a surface of the test strip having a membrane impregnated with a color-producing reagent;
- measuring a temperature and measuring a second reflectance at about a second wavelength;
- determining a second glucose concentration based on the second reflectance at about the second wavelength and the measured temperature with the equation of the form:

$$G2=a0+a1*G1+a2*T+a3*K/S_{\lambda 2}+a4*G1*K/S_{\lambda 2}+a5*G1*T$$

where:
- G2 is the second glucose concentration corrected for temperature and hematocrit effects;
- G1 is the first glucose concentration and is determined from the reflectance measured at about a first wavelength, λ1;
- T is temperature;
- $K/S_{\lambda 2}$ comprises a value obtained with an equation of the form:

$$K/S_{\lambda 2}=(1-R_2)^2/(2*R_2)$$

where:
- $R_2$ is the second reflectance at about the second wavelength, λ2, taken at an endpoint time; and
- Coefficients a0 through a5 depend on the endpoint time at which the first reflectance at first wavelength, λ1, is measured; and
- displaying the second glucose concentration.

6. The method of any one of claims 1 and 3, wherein the first wavelength ranges from about 600 nm to about 700 nm and the second wavelength ranges from about 800 nm to about 1100 nm.

7. The method of any one of claims 1 and 3, wherein the first wavelength is about 660 nm and the second wavelength is about 940 nm.

8. The method of any one of claims 1 and 3, in which the determining of one of the first and second glucose concentration comprises calculating with a microprocessor.

* * * * *